(12) United States Patent
Ariav et al.

(10) Patent No.: US 7,716,988 B2
(45) Date of Patent: May 18, 2010

(54) APPARATUS FOR USE IN CONTROLLING SNORING AND SENSOR UNIT PARTICULARLY USEFUL THEREIN

(75) Inventors: Arie Ariav, Doar-Na Hof Ashkelon (IL); Vladimir Ravitch, Ashkelon (IL)

(73) Assignee: Nexense Ltd., Yavne (IL)

( * ) Notice: Subject to any disclaimer, the term of this patent is extended or adjusted under 35 U.S.C. 154(b) by 445 days.

(21) Appl. No.: 11/657,006

(22) Filed: Jan. 24, 2007

(65) Prior Publication Data

US 2007/0277835 A1   Dec. 6, 2007

(30) Foreign Application Priority Data

May 30, 2006   (IL)   .................................. 176025

(51) Int. Cl.
 *G01N 29/024*   (2006.01)
(52) U.S. Cl. ...................... 73/597; 73/602; 73/862.454; 73/862.471
(58) Field of Classification Search ............ 73/862.046, 73/862.68, 597, 602, 862.454, 862.471; 310/364, 800
See application file for complete search history.

(56) References Cited

U.S. PATENT DOCUMENTS

| | | | |
|---|---|---|---|
| 4,741,214 A | 5/1988 | Vidmantas | |
| 5,113,646 A | 5/1992 | Cox | |
| 5,209,126 A * | 5/1993 | Grahn | .................... 73/862.046 |
| 5,435,317 A | 7/1995 | McMahon et al. | |
| 5,458,105 A | 10/1995 | Taylor et al. | |
| 5,844,996 A | 12/1998 | Enzmann et al. | |

(Continued)

FOREIGN PATENT DOCUMENTS

DE   102007006467   3/2008

(Continued)

OTHER PUBLICATIONS

International Preliminary Report on Patentability Dated Jan. 29, 2009 From the International Bureau of WIPO Re.: Application No. PCT/IL2007/000635.

(Continued)

*Primary Examiner*—J M Saint Surin
(74) *Attorney, Agent, or Firm*—Daniel J. Swirsky; AlphaPatent Associates Ltd.

(57) ABSTRACT

Apparatus for use in controlling snoring, including: a sensor system for sensing snoring by a person while sleeping, and a stimulus device effective, when actuated by the sensor system, to apply a stimulus to the person for producing a response tending to interrupt the person's snoring. The stimulus device includes a vibrator and a band for enclosing a body part of the person and for applying a vibration to the body part. Also described is a force or displacement sensor, which includes a housing filled with a liquid having high transmissivity and low attenuation properties with respect to acoustical waves, and an acoustical transmitter and an acoustical receiver carried by opposed walls of the housing spaced from each other to define between them an acoustical transmission channel of the liquid. The housing is deformable by a force such as to change the length of the acoustical transmission channel in accordance with the applied force. A measuring system measures the transit time of an acoustical wave through the acoustical transmission channel to provide a measurement of the applied force.

17 Claims, 6 Drawing Sheets

U.S. PATENT DOCUMENTS

| | | | |
|---|---|---|---|
| 5,987,983 A * | 11/1999 | Ariav et al. | ............ 73/488 |
| 5,989,193 A | 11/1999 | Sullivan | |
| 6,057,767 A | 5/2000 | Barnoach | |
| 6,371,120 B1 | 4/2002 | Chiu et al. | |
| 6,468,234 B1 | 10/2002 | Van der Loos et al. | |
| 6,491,647 B1 | 12/2002 | Bridger et al. | |
| 6,544,199 B1 | 4/2003 | Morris | |
| 6,621,278 B2 | 9/2003 | Ariav | |
| 6,640,631 B1 | 11/2003 | Toda | |
| 6,716,169 B2 | 4/2004 | Muramatsu et al. | |
| 6,865,359 B2 * | 3/2005 | Sasaki et al. | ............ 399/237 |
| 6,984,207 B1 | 1/2006 | Sullivan et al. | |
| 7,290,451 B2 | 11/2007 | Taniguchi et al. | |
| 2003/0236467 A1 | 12/2003 | Alfini | |
| 2006/0059999 A1 | 3/2006 | Foller | |
| 2008/0306396 A1* | 12/2008 | Ariav et al. | ............ 600/527 |

FOREIGN PATENT DOCUMENTS

| | | |
|---|---|---|
| GR | 1003643 | 8/2001 |
| WO | WO 03/057304 | 7/2003 |
| WO | WO 2004/043249 | 5/2004 |
| WO | WO 2004/082549 | 9/2004 |
| WO | WO 2007/138575 | 12/2007 |

OTHER PUBLICATIONS

International Search Report Dated Aug. 11, 2008 From the International Searching Authority Re.: Application No. PCT/IL07/00635.

* cited by examiner

APPARATUS FOR USE IN CONTROLLING SNORING AND SENSOR UNIT PARTICULARLY USEFUL THEREIN

RELATED APPLICATIONS

This Application claims the benefit of Israel Patent Application No. 176025 filed on May 30, 2006, the contents of which are hereby incorporated by reference.

FIELD AND BACKGROUND OF THE INVENTION

The present invention relates to apparatus for controlling snoring, and also to a sensor unit particularly useful in such apparatus.

It is generally recognized that snoring not only unduly disturbs those in the immediate vicinity, but probably more important, may be an indication of a serious sleep disorder which can lead to strokes, heart diseases, hypertension, etc. Many sound-type sensors have been developed for this purpose, but such sensors are also sensitive to sounds other than snoring sounds, and are therefore generally subject to a relatively high rate of false alarms.

International Application No. PCT/IL2005/000617, published under International Publication No. WO2005/120167, assigned to the same assignee as the present application, discloses apparatus for controlling snoring by a person utilizing sensor units which sense mechanical vibrations of an external part of the person's body, and which, therefore, are less sensitive to sounds other than snoring sounds.

OBJECTS AND BRIEF SUMMARY OF THE PRESENT INVENTION

An object of the present invention is to provide apparatus for controlling snoring having a number of advantages over the apparatus described in the above-cited International Application. Another object of the invention is to provide a novel force or displacement sensor having a high level of sensitivity especially in the presence of various ambient conditions, and therefore particularly useful in apparatus for controlling snoring.

According to one aspect of the present invention, there is provided apparatus for use in controlling snoring, comprising: a sensor system for sensing snoring by a person while sleeping; and a stimulus device effective, when actuated by the sensor system sensing snoring in the person, to apply a stimulus to the person for producing a response tending to interrupt the person's snoring; the stimulus device including a vibrator and a band for enclosing a body part of the person and for applying a vibration to the body part.

In the described preferred embodiment, the vibrator includes a battery-powered motor-driven eccentric weight.

As will be described more particularly below, the foregoing features of the invention are particularly useful in apparatus for controlling snoring of two persons, since the apparatus can selectively sense snoring by either of the two persons and selectively apply the stimulus to the one determined to be snoring.

According to another aspect of the present invention, there is provided a force or displacement sensor unit, particularly useful in the above anti-snoring apparatus, which sensor unit comprises: a housing filled with a liquid having high transmissivity and low attenuation properties with respect to acoustical waves; an acoustical transmitter and an acoustical receiver carried by opposed walls of the housing spaced from each other so as to define between the transmitter and receiver, an acoustical transmission channel of the liquid; the housing being deformable by a force applied to it such as to change the length of the acoustical transmission channel between the transmitter and receiver in accordance with the applied force; and a measuring system for measuring the transit time of an acoustical wave from the transmitter to the receiver via the acoustical transmission channel to provide a measurement of the applied force.

As will also be described below, such a sensor is capable of providing a very high degree of sensitivity in detecting snoring, in determining the person doing the snoring, and in applying the stimulus to such person, even in the presence of ambient conditions.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
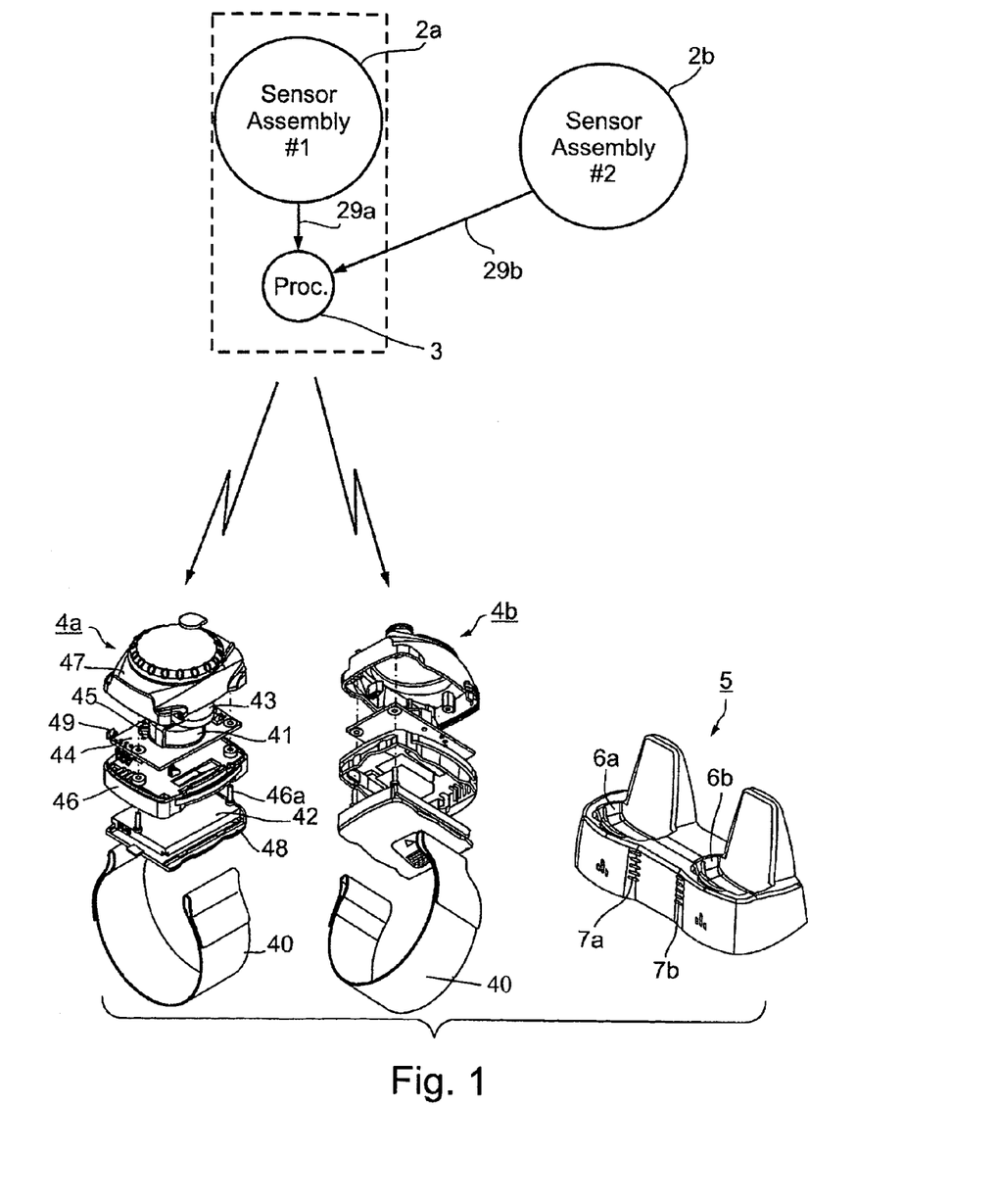
FIG. 1 is a block diagram illustrating the main components in one form of apparatus constructed in accordance with the present invention for controlling snoring by two persons.

Reference is first made to FIG. 1 illustrating, in block diagram form, the main components of one form of apparatus constructed in accordance with the present invention for controlling snoring, in this case for controlling snoring by two persons.

The illustrated apparatus includes two sensor assemblies 2a, 2b, each for sensing a snoring condition by a respective person. Sensor assembly 2a is a master assembly and includes a processor unit 3 for receiving the outputs of the two sensor assemblies 2a, 2b and for determining whether either indicates a snoring condition. The illustrated apparatus further includes two stimulus devices 4a, 4b, one worn by each of the two persons and activated by the processor unit 3 when determining that a snoring condition is present in the respective person. The two sensor assemblies 2a, 2b are constructed as separate units for introduction over, under or within the mattress or mattresses of the respective persons; whereas the two stimulus devices 4a, 4b are constructed to be worn on the wrist or foot of the respective person.

Figure 2:
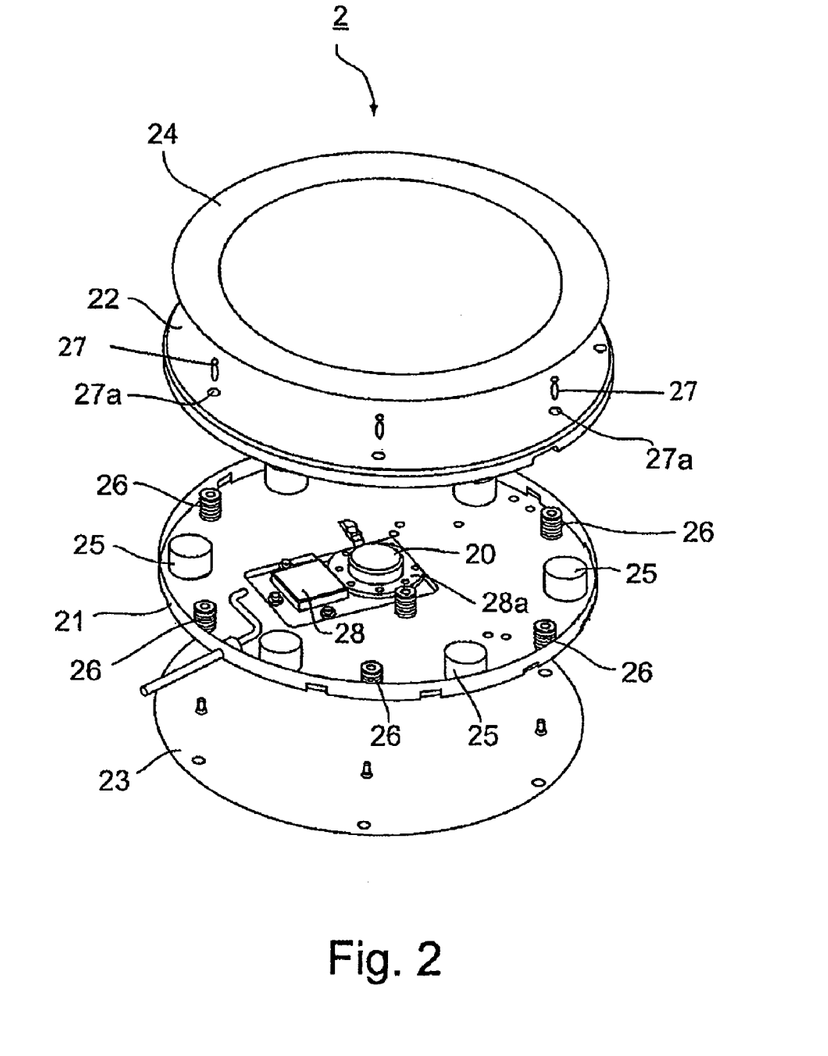
FIG. 2 is an exploded view of one of the two sensor assemblies in the apparatus of FIG. 1.
Figure 3:
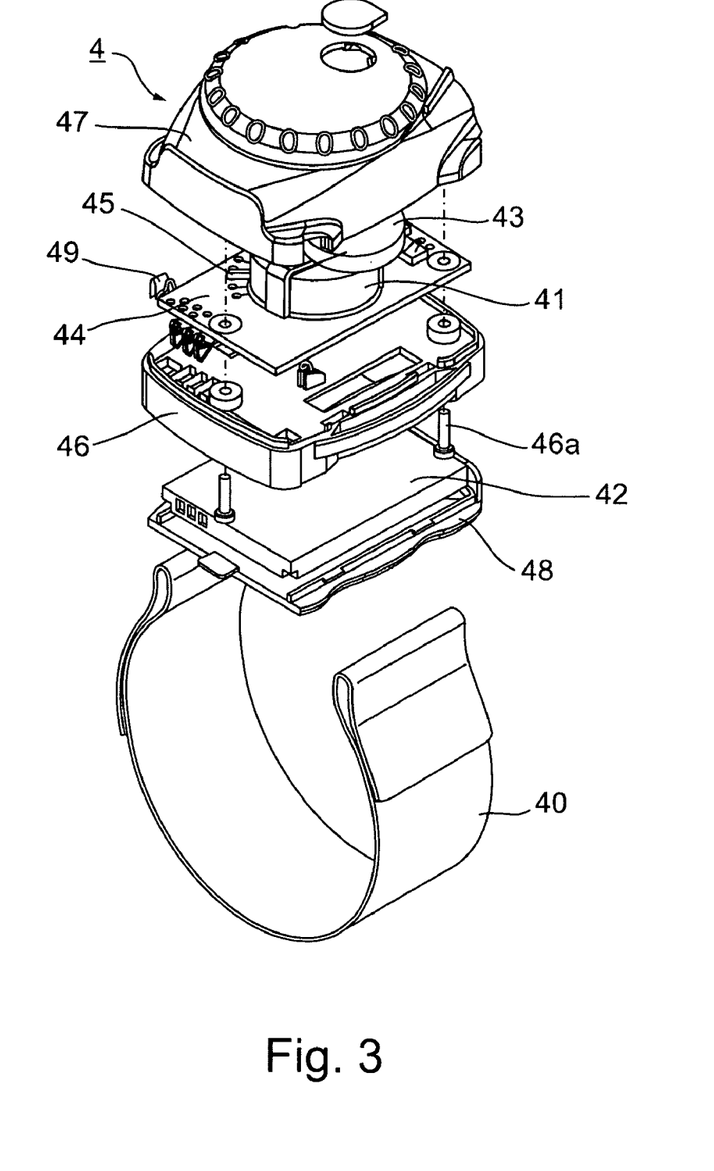
FIG. 3 is an exploded view of one of the two stimulus devices in the apparatus of FIG. 1.

FIG. 2 more particularly illustrates the construction of each of the two sensor assemblies 2a, 2b; whereas FIG. 3 more particularly illustrates the construction of each of the stimulus devices 4a, 4b. As will be described more particularly below, each of the stimulus devices 4a, 4b, when activated upon sensing a snoring condition, produces a stimulus which is applied to the person such as to produce a response in the person tending to interrupt the person's snoring.

The apparatus illustrated in FIG. 1 further includes a charger device 5 having two sockets 6a, 6b for recording information from the two stimulus devices 4a, 4b when not worn by the respective person, and for charging the batteries. The charger device also includes an indicator or display 7a, 7b for each person, which displays information as to the number of snoring episodes determined by the apparatus to have been experienced by each person during a particular sleeping period, e.g., night of sleep. Displays 7a, 7b may each be in the form of vertically-aligned light bars, for providing information as to the number of snoring episodes experienced by the respective user. Charger device 5 receives this information from its respective stimulus device 4a, 4b when inserted in the respective socket 6a, 6b.

The construction of each of the sensor assemblies 2a, 2b is illustrated in FIG. 2, and therein generally designated 2. It includes a sensor unit 20 mounted centrally of and between a lower circular plate 21 and an upper circular plate 22, such that any force applied to the upper plate 22 is transferred to the sensor unit 20. The two plates 21, 22 are in turn covered by a lower cover 23 and an upper cover 24. As indicated earlier, sensor assembly 2a is the master unit and also includes the processor 3.

Each sensor assembly 2a and 2b further includes a plurality of resilient pads 25 alternating with a plurality of elastic springs 26 located between the sensor unit and the outer periphery of the two circular plates 21, 22. The resilient pads 25 are preferably of a material having high damping characteristics with respect to mechanical vibrations. Examples of such materials suitable for the resilient pads are soft sponge rubber and a soft silicon elastomer.

The upper plate 22 is supported on the sensor unit 20, as well as on the resilient pads 25 and springs 26, such that any force applied to the upper plate is transmitted to the sensor unit. The upper plate 22 is thus free to move vertically with respect to the lower plate 21. The upper plate 22 is guided in its movements by a plurality of screws 27 fixed to the lower plate 21. Screws 27 freely pass through openings 27a in the upper plate 22 and have enlarged heads engageable with the upper surfaces of the upper plate 22.

The construction of sensor unit 20 is more particularly described below with respect to FIGS. 4-7.

Each sensor assembly 2 further includes a measuring circuit 28 carried by a printed circuit board 28a for receiving the output of the respective sensor unit, and for transmitting it to the processor 3 via conductors 29a, 29b (FIG. 1). Processor unit 3 thus receives the outputs of the two sensor assemblies 2a, 2b and processes them in order to determine whether either output indicates a snoring condition existing in the person being monitored by the respective sensor assembly. If snoring is indicated, processor 3 activates, preferably in a wireless manner, the respective stimulus device 4a, 4b, of the person whose sensor assembly indicates a snoring condition.

Each stimulus device 4a, 4b, to be worn by the respective person, is more particularly shown in FIG. 3 wherein the stimulus device is generally designated 4. Each stimulus device includes a wrist band 40 to be worn by the respective person, and a small electrical motor 41 powered by a battery 42 for rotating an eccentric weight 43 when the battery is energized. The motor 41 is mounted for rotation on a printed circuit board 44 which includes a presettable control 45 for presetting the rotary speed of the motor, and thereby the intensity of the stimulus produced by the eccentric weight 43 when rotated by the motor.

The motor and eccentric-weight are mounted on a base 46 by fasteners 46a, which base is insertable into a socket 6a, 6b in charger device 5 (FIG. 1). The upper side of each stimulator device 4 is closed by a cover plate 47, and the lower side by a cover plate 48. The assembly including motor 41, battery 42 eccentric weight 43 and base 46 are attachable to wrist band 40, and are removable therefrom for charging the battery when the device is not worn, by insertion into a socket 6a, 6b of charger device 5. For this purpose, the printed circuit board 44 includes contacts 49 engageable with contacts in the charger device when inserted into the respective socket of the charger device.

FIGS. 4-7 illustrate preferred constructions of sensor unit 20 which may be used in each sensor assembly 2a, 2b in the apparatus of FIGS. 1-3.

Figure 4:
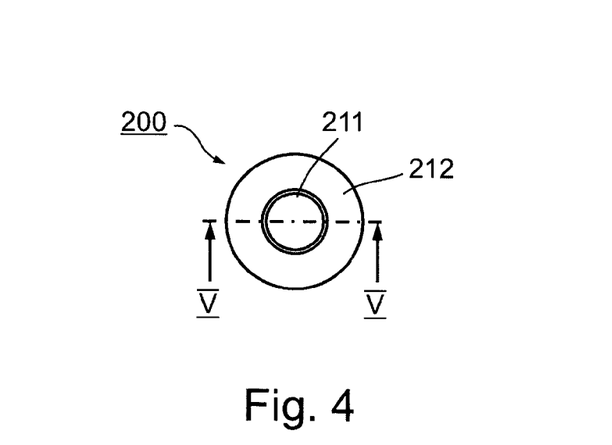
FIG. 4 is a plan view illustrating one form of sensor constructed in accordance with the present invention for use in the sensor assembly of FIG. 2.
Figure 5:
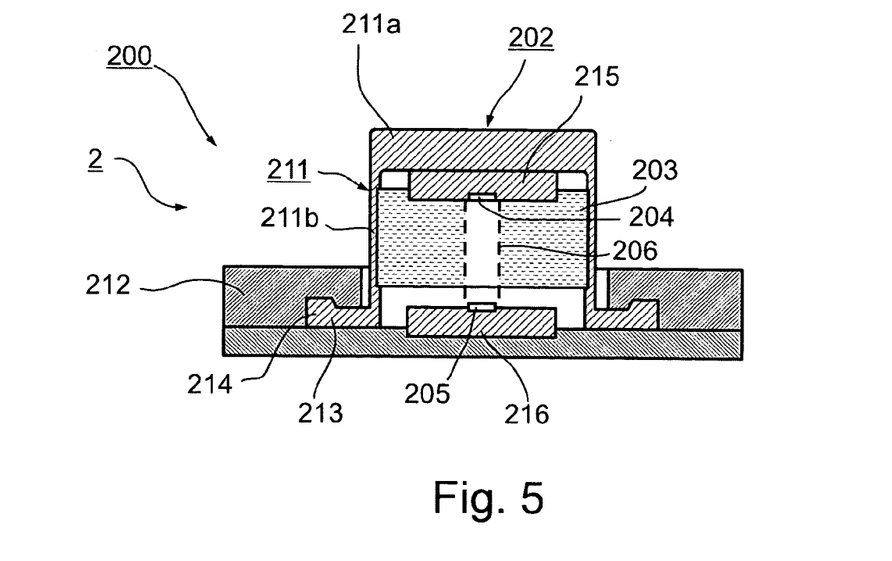
FIG. 5 is an enlarged sectional view along lines V-V of FIG. 4.

The sensor unit illustrated in FIGS. 4 and 5 is generally designated 200. It includes a housing 202 filled with a liquid 203 having high transmissivity and low attenuation properties with respect to acoustical waves. Preferably, liquid 203 is a silicone oil having high viscosity properties, similar to honey.

The illustrated sensor further includes an acoustical transmitter 204 and an acoustical receiver 205 carried on opposed walls of housing 202, spaced from each other so as to define, between transmitter 204 and receiver 205, an acoustical transmission channel 206 constituted of the liquid 203. As will be described more particularly below, housing 202 is deformable by a force applied to it such as to change the length of acoustical transmission channel 206 in accordance with the applied force. Thus, a precise measurement of the transit time of an acoustical wave from transmitter 204 to receiver 206 provides an accurate measurement of the applied force.

As shown in FIG. 5, housing 202 is constituted of a main section 211 in the configuration of a hollow button open at one end (its lower end), and a closure section 212 closing the open end of the main section 211. As shown particularly in FIG. 4, the main section 211 is of circular configuration in cross-section, and closure section 212 is also of circular configuration but of larger diameter than that of the main section. Main section 211 of housing 202 is formed with an outwardly-extending peripheral flange 213 (FIG. 5) circumscribing its open end; and closure section 212 is formed with an annular recess 214 for receiving the peripheral flange 213.

Section 211 of housing 202 is preferably made of a material, such as rubber, which has high attenuation properties with respect to acoustical waves, whereas housing section 212 is made of metal and has no direct contact with acoustical waves.

Main section 211 of housing 202 is formed with a relatively thick end wall 211a, and with a much thinner side wall 211b between end wall 211a and its peripheral flange 213. Side wall 211b of the housing is sufficiently thin so as to be easily deformable by a force applied to end wall 211a, such that the displacement of transmitter 204 carried by end wall 211a of housing 202 towards receiver 205 carried by the opposed end wall 212 of housing 202, provides a measurement of the applied force.

In the embodiment illustrated in FIG. 5, the transmitter 204 and receiver 205 are mounted on damper members 215 and 216, respectively, fixed to the opposite ends of housing 202. Damper members 215, 216 are also made of a material, such as rubber, having high attenuation properties with respect to acoustical waves. Such damper members thus minimize reflections of the acoustical waves outside of the acoustical transmission channel 206.

Figure 6:
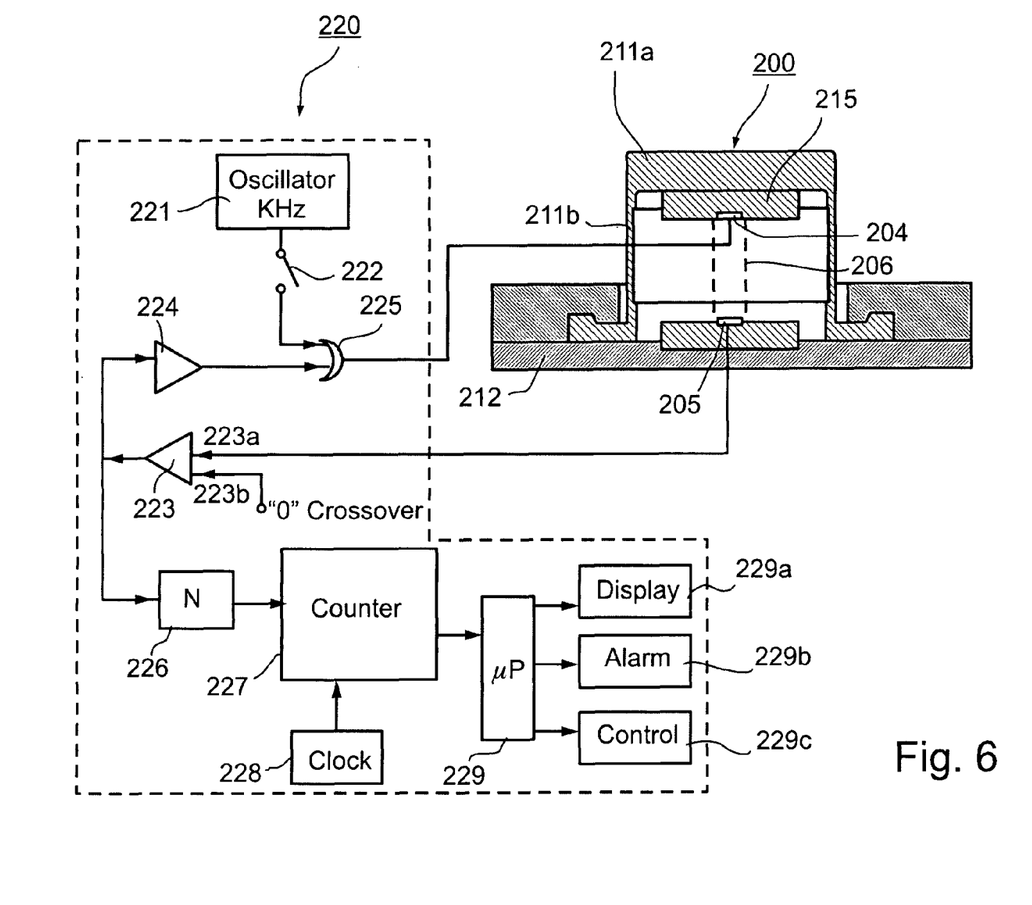
FIG. 6 illustrates a measuring system for using the sensor of FIGS. 4 and 5 in order to measure mechanical vibrations, or other forms of force or displacement in a highly sensitive manner.

FIG. 6 more particularly illustrates a preferred circuit, generally designated 220, according to U.S. Pat. No. 6,621,278 and International Patent Application PCT/IL05/000617, which is preferably used with the force sensor of FIGS. 4 and 5 to produce a very precise measurement of the force applied to end wall 211a of sensor housing 202. Briefly, such a system operates by: (a) transmitting from transmitter 204 a cyclically-repeating energy wave through the transmission channel 206 defined with receiver 205; (b) changing the frequency of the transmission while maintaining the number of waves in the loop including the acoustical transmission channel as a whole integer; and (c) utilizing the changes in frequency of the transmission to provide an indication of the deformation of the force applied.

In the described preferred embodiment, operation (b) includes: detecting a predetermined fiducial point in each cyclically-repeating energy wave received by receiver 205; and continuously changing the frequency of the transmission in accordance with the detected fiducial point of each received energy wave such that the number of energy waves in the loop of the transmission channel is a whole integer.

More particularly, the system illustrated in FIG. 6 operates as follows: Initially, oscillator 221 is energized while switch 222 is closed so as to cause transmitter 204 to transmit a succession of sonic pulses until such pulses are received by receiver 205. Once the pulses are received by receiver 205, switch 222 is opened so that the pulses received by receiver 205 are thereafter used for controlling the transmitter 204.

As shown in FIG. 6, the sonic signals received by receiver 205 are fed to a comparator 223 via its input 223a. Comparator 223 includes a second input 223b connected to a predetermined bias so as to detect a predetermined fiducial or reference point in the received signal. In the example illustrated in FIG. 6, this predetermined fiducial point is the "zero" cross-over point of the received signal; therefore, input 223b of comparator 223 is at a zero bias.

The output of comparator 223 is fed to an amplifier 224, e.g., a monostable oscillator, which is triggered to produce an output signal at each fiducial point (zero cross-over point) in the signals received by receiver 205. The outputs from amplifier 224 are fed via an OR-gate 225 to trigger the transmitter 204 for the next sonic pulse. Since switch 222 is open, transmitter 204 will thus be triggered by each signal received by the receiver 205 to transmit the next sonic pulse in the succession of pulses.

It will thus be seen that the frequency of the output pulses or signals from transmitter 205 will change with a change in the spacing between the transmitter 204 and receiver 205. It will also be seen that the number of wavelengths or pulses in the loop including transmitter 204 and receiver 205 will be a whole integer. This change in frequency by the transmitter 4, while maintaining the number of waves between the transmitter and receiver 205 as a whole integer, enables a precise determination to be made of the distance between the transmitter and receiver, and thereby of the deformation of membrane 211.

A summing circuit, including counter 226, counter 227, clock 228 and microprocessor 229, enables the detected frequency difference, and thereby the measurement precision, to be increased by a factor "N". Thus, the precision of the measurement can be preset, almost without limitation, by the selection of the appropriate frequency, clock rate for clock 228, and summation factor "N" for counter 227.

As further shown in FIG. 6, the output from microprocessor 229 of the control and processor circuit 220 may be used for display, alarm and/or control purposes, as schematically shown at 229a, 229b and 229c. In this case, the outputs of the two sensor assemblies 2a, 2b (FIG. 1) are applied to processor 3, which processes them to determine whether a snoring condition was found to exist. The processing may be done according to the above-cited International Patent Application No. PCT/IL2005/000617.

Further details of the construction and operation of such measuring and processing circuits are described in U.S. Pat. No. 6,621,278 and International Patent Application PCT/IL05/000617, the contents of which are incorporated herein by reference.

Figure 7:
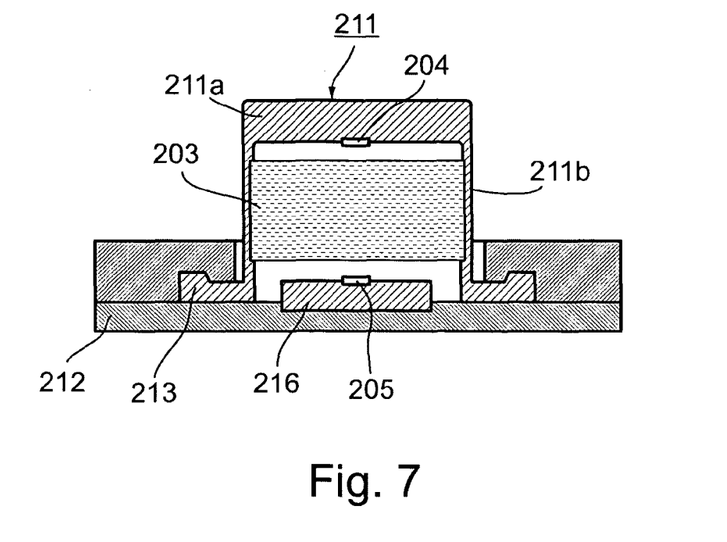
FIG. 7 is a view similar to that of FIG. 5 but illustrating a modification in the construction of the sensor.

FIG. 7 illustrates a modification wherein damper member 215 is omitted, and the transmitter 204 is directly mounted to the inner face of end wall 211a of housing 202. In all other respects, the construction illustrated in FIG. 7 is the same and operates in the same manner as described above.

Figure 8:
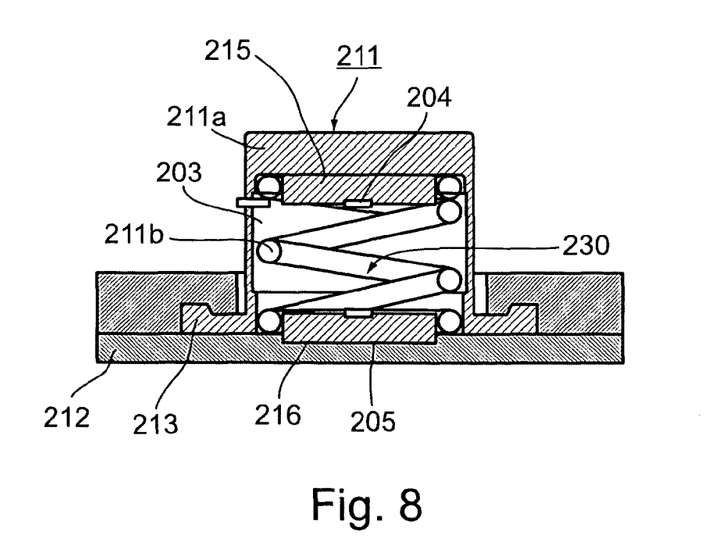
FIG. 8 is a view similar to that of FIG. 5 but illustrating the inclusion of a coiled spring in order to reduce the response time of the sensor.

FIG. 8 illustrates a further variation, wherein a coiled spring 230 is interposed between the opposed walls of housing 202 effective to bias the opposed walls apart. The provision of such a spring adds a specific resonance to the sensor; and by applying a constant positive pressure between the opposed walls of the housing, the spring reduces the response time of the sensor.

While the invention has been described with respect to several preferred embodiments, it will be appreciated that these are set forth merely for purposes of example, and that many other variations, modifications and applications of the invention may be made.

What is claimed is:

1. A force or displacement sensor, comprising:
   a housing enclosure filled with a liquid having high transmissivity and low attenuation properties with respect to acoustical waves;
   an acoustical transmitter and an acoustical receiver carried by opposed walls of said housing spaced from each other so as to define between said transmitter and receiver, an acoustical transmission channel of said liquid;
   said housing being deformable by a force applied to it such as to change the length of said acoustical transmission channel between said transmitter and receiver in accordance with the applied force;
   and a measuring system for measuring the transit time of an acoustical wave from said transmitter to said receiver via said acoustical transmission channel to provide a measurement of said applied force.

2. The sensor according to claim 1, wherein said liquid has high viscosity properties similar to honey.

3. The sensor according to claim 1, wherein said liquid is a silicone oil.

4. The sensor according to claim 1, wherein said housing is made of a deformable material.

5. The sensor according to claim 1, wherein said transmitter and receiver are each mounted on a damper member having high damping properties to acoustical waves.

6. The sensor according to claim 1, wherein said housing is constituted of a main section in the configuration of a hollow button open at one end, and a closure section closing the open end of said main section.

7. The sensor according to claim 6, wherein the open end of said main section is formed with an outwardly-extending peripheral flange, and said closure section includes an annular recess receiving said peripheral flange.

8. The sensor according to claim 6, wherein said main section of the housing is of circular configuration in cross-section, and said closure section of the housing is of circular configuration of larger diameter than the diameter of said main section.

9. The sensor according to claim 1, wherein said housing includes a coiled spring interposed between said opposed walls of the housing effective to bias said opposed walls apart.

10. The sensor according to claim 1, wherein said measuring system comprises a processor for changing the frequency of the acoustical waves transmitted by said transmitter to said receiver via said acoustical transmission channel, while maintaining the number of waves in a loop including said acoustical transmission channel as a whole integer irrespective of changes in said applied force; and for utilizing the changes in frequency to produce a measurement of said transit time, and thereby of said applied force.

11. Apparatus including a sensor according to claim 1, wherein said sensor is in a sensor assembly which further includes a pair of plates of larger size than said sensor and physically contacting the opposite sides of said sensor housing.

12. The apparatus according to claim 11, wherein said sensor assembly also includes a plurality of resilient pads alternating with a plurality of elastic springs located between said sensor and the outer peripheries of said pair of plates.

13. Apparatus for use in controlling a sleep event, comprising:
a sensor system including a sensor according to claim 1 for sensing the sleep event by a person while sleeping;
a stimulus device effective, when actuated by the sensor system sensing the sleep event in the person, to apply a stimulus to the person for producing a response tending to interrupt said sleep event;
and a processor for processing the output of said sensor assembly and for activating said stimulus device when the output indicates said sleep event;
said stimulus device including a vibrator and a band for enclosing a body part of the person and for applying a vibration to said body part.

14. The apparatus according to claim 13, wherein said stimulus device further includes a battery for powering said motor, and said sensor system communicates with said stimulus device via a wireless transmitter and receiver.

15. The apparatus according to claim 14, wherein said system further includes a charger device constructed to receive the stimulus device when not worn by the person in order to recharge the battery therein, said charger device also including a display for displaying information indicating the number of times said sleep event was sensed during a predetermined time period.

16. The apparatus according to claim 15, wherein said sensor system further comprises a second, battery-powered sensor assembly communicating with said processor via a second wireless transmitter and receiver for sensing a said sleep event by a second person; and a second stimulus device to be worn by the second person for applying a stimulus to the second person when a said sleep event is indicated to be present in the second person; said charger device being constructed to receive also the second stimulus device for charging its battery when not worn by the second person, and also for displaying information indicating the number of times a sleep event by the second person was sensed during a predetermined time period.

17. The apparatus according to claim 16, wherein the two sensor assemblies are constituted of two separate units each constructed to be received under, over or within a mattress of the respective person; and wherein said processor is included in one of said sensor assemblies.

* * * * *